US012753132B2

(12) United States Patent
Pretz et al.

(10) Patent No.: US 12,753,132 B2
(45) Date of Patent: Oct. 6, 2026

(54) SYSTEMS AND METHODS FOR PRODUCING OLEFINS

(71) Applicant: Dow Global Technologies LLC, Midland, MI (US)

(72) Inventors: Matthew T. Pretz, Freeport, TX (US); Donald F. Shaw, Forked River, NJ (US); Richard Edwards Walter, Long Valley, NJ (US); Fermin Alejandro Sandoval, Houston, TX (US)

(73) Assignee: Dow Global Technologies LLC, Midland, MI (US)

( * ) Notice: Subject to any disclaimer, the term of this patent is extended or adjusted under 35 U.S.C. 154(b) by 175 days.

(21) Appl. No.: 18/257,329

(22) PCT Filed: Dec. 14, 2021

(86) PCT No.: PCT/US2021/063293

§ 371 (c)(1),
(2) Date: Jun. 14, 2023

(87) PCT Pub. No.: WO2022/132758

PCT Pub. Date: Jun. 23, 2022

(65) Prior Publication Data

US 2024/0034700 A1 Feb. 1, 2024

Related U.S. Application Data

(60) Provisional application No. 63/126,095, filed on Dec. 16, 2020.

(51) Int. Cl.

*C07C 5/32* (2006.01)
*B01D 45/16* (2006.01)

(Continued)

(52) U.S. Cl.

CPC .............. *C07C 5/325* (2013.01); *B01D 45/16* (2013.01); *B01J 8/0055* (2013.01); *B01J 8/1827* (2013.01);

(Continued)

(58) Field of Classification Search

None

See application file for complete search history.

(56) References Cited

U.S. PATENT DOCUMENTS 3,475,326 A 10/1969 Luckenbach
3,645,992 A 2/1972 Elston (Continued)

FOREIGN PATENT DOCUMENTS

CA 2073842 A1 6/1993
CN 104437274 B 3/2015

(Continued)

OTHER PUBLICATIONS

Sadeghbeigi, Reza. (2012). Fluid Catalytic Cracking Handbook Chapter 11 pp. 223, 224, 239, 240 Elsevier. https://app.knovel.com/hotlink/pdf/id:kt009IVL13/fluid-catalytic-cracking/refractory-quality (Year: 2012).*

(Continued)

*Primary Examiner* — Renee Robinson
*Assistant Examiner* — Alyssa L Cepluch
(74) *Attorney, Agent, or Firm* — Dinsmore & Shohl LLP

(57) ABSTRACT

According to one or more embodiments, olefins may be produced by contacting a hydrocarbon feed stream with a particulate solid in a reaction vessel. The reaction vessel may be connected to a riser. The riser may extend through a riser port of an outer shell of a particulate solid separation section such that the riser may comprise an interior riser segment and an exterior riser segment. The particulate solid separation section may include a gas outlet port, a riser port, (Continued)

and a particulate solid outlet port. The particulate solid separation section may house a gas/solids separation device and a solid particulate collection area. The riser port may be positioned on a sidewall of the outer shell such that it is not located on a central vertical axis of the particulate solid separation section. The particulate solid may be separated from an olefin-containing product stream in the gas/solids separation device.

18 Claims, 6 Drawing Sheets

(51) Int. Cl.

| | |
|---|---|
| ***B01J 8/00*** | (2006.01) |
| ***B01J 8/18*** | (2006.01) |
| ***B01J 8/26*** | (2006.01) |
| ***C07C 1/24*** | (2006.01) |

(52) U.S. Cl.

CPC *B01J 8/26* (2013.01); *C07C 1/24* (2013.01); *B01J 2208/00769* (2013.01)

(56) References Cited

U.S. PATENT DOCUMENTS

| | | | |
|---|---|---|---|
| 3,914,342 | A | 10/1975 | Mitchell |
| 4,076,698 | A | 2/1978 | Anderson et al. |
| 4,502,947 | A | 3/1985 | Haddad et al. |
| 4,547,341 | A | 10/1985 | Weber |
| 4,579,716 | A | 4/1986 | Krambeck et al. |
| 4,588,558 | A | 5/1986 | Kam et al. |
| 4,599,392 | A | 7/1986 | McKinney et al. |
| 4,725,410 | A | 2/1988 | Krug et al. |
| 5,156,817 | A | 10/1992 | Luckenbach |
| 5,190,650 | A | 3/1993 | Tammera et al. |
| 5,272,236 | A | 12/1993 | Lai et al. |
| 5,275,641 | A | 1/1994 | Tammera et al. |
| 5,278,272 | A | 1/1994 | Lai et al. |
| 5,368,721 | A | 11/1994 | Terry et al. |
| 5,540,893 | A | 7/1996 | English |
| 5,582,923 | A | 12/1996 | Kale et al. |
| 5,733,155 | A | 3/1998 | Sagawa |
| 5,854,045 | A | 12/1998 | Fang et al. |
| 6,857,814 | B2 | 2/2005 | Jensen |
| 7,272,204 | B2 | 9/2007 | Jensen |
| 7,476,428 | B2 | 1/2009 | Burki et al. |
| 8,669,406 | B2 | 3/2014 | Pretz et al. |
| 9,695,306 | B2 | 7/2017 | Ambroise |
| 9,802,394 | B2 | 10/2017 | Cavacas et al. |
| 10,357,913 | B2 | 7/2019 | Dou et al. |
| 2004/0076554 | A1 | 4/2004 | Kuechler et al. |
| 2006/0130443 | A1 | 6/2006 | Dirkse et al. |
| 2008/0050545 | A1 | 2/2008 | Harvey |
| 2009/0155584 | A1 | 6/2009 | Rolland et al. |
| 2009/0283445 | A1 | 11/2009 | Tammera et al. |
| 2012/0028058 | A1 | 2/2012 | Paolilli et al. |
| 2012/0234725 | A1 | 9/2012 | Palmas et al. |
| 2017/0361295 | A1 | 12/2017 | Pretz et al. |
| 2018/0134012 | A1 | 5/2018 | Barreneche |
| 2019/0314782 | A1 | 10/2019 | Pretz et al. |
| 2020/0231521 | A1 | 7/2020 | Pretz et al. |
| 2020/0346177 | A1* | 11/2020 | Amblard ................ B01J 8/0055 |

FOREIGN PATENT DOCUMENTS

| | | | | | |
|---|---|---|---|---|---|
| EP | 1046696 | A2 | | 10/2000 | |
| EP | 1628774 | B1 | | 4/2012 | |
| EP | 2064057 | B1 | | 3/2017 | |
| EP | 3227370 | B1 | | 11/2019 | |
| JP | 1954001975 | B | | 4/1954 | |
| JP | H10-311893 | | | 11/1998 | |
| JP | 2000233471 | A | | 8/2000 | |
| JP | 5479067 | B2 | | 4/2014 | |
| JP | 2014175121 | A | | 9/2014 | |
| JP | 2020519487 | A | | 7/2020 | |
| WO | 1995000603 | A1 | | 1/1995 | |
| WO | 2007117384 | A1 | | 10/2007 | |
| WO | 2015173199 | A1 | | 11/2015 | |
| WO | 2017139031 | A1 | | 8/2017 | |
| WO | 2017186953 | A1 | | 11/2017 | |
| WO | 2018069029 | A1 | | 4/2018 | |
| WO | 2018071513 | A1 | | 4/2018 | |
| WO | 2018200366 | A1 | | 11/2018 | |
| WO | WO-2019027870 | A1 | * | 2/2019 | ............ B01J 8/1809 |
| WO | WO-2019091736 | A1 | * | 5/2019 | ............ B01J 8/0055 |
| WO | 2019126189 | A1 | | 6/2019 | |
| WO | 2019191825 | A1 | | 10/2019 | |
| WO | 2019243456 | A1 | | 12/2019 | |
| WO | 2020009860 | A1 | | 1/2020 | |
| WO | 2020046978 | A1 | | 3/2020 | |
| WO | 2020112148 | A1 | | 4/2020 | |
| WO | 2020167929 | A1 | | 8/2020 | |
| WO | 2020263884 | A1 | | 12/2020 | |
| WO | WO-2021024119 | A1 | * | 2/2021 | ............ C10G 11/18 |
| WO | 2021118739 | A1 | | 6/2021 | |

OTHER PUBLICATIONS

Grace et al. "Introduction to circulating fluidized beds" Circulating Fluidized Beds (1997) pp. 1-20 (Year: 1997).*

International Search Report and Written Opinion dated Apr. 8, 2022, pertaining to Int'l Patent Application No. PCT/US2021/063293.

International Search Report and Written Opinion dated Mar. 29, 2022, pertaining to Int'l Patent Application No. PCT/US2021/063220.

International Search Report and Written Opinion dated Mar. 14, 2022, pertaining to Int'l Patent Application No. PCT/US2021/063211.

International Search Report and Written Opinion dated Mar. 14, 2022, pertaining to Int'l Patent Application No. PCT/US2021/063221.

Saudi Arabian Substantive Examination Report dated Apr. 7, 2024, pertaining to SA Patent Application No. 523441058, 5 pgs.

Russian Office Action dated Apr. 22, 2024, pertaining to RU Patent Application No. 2023117790, 14 pgs.

Saudi Arabian Substantive Examination Report dated Mar. 19, 2024, pertaining to SA Patent Application No. 523441242, 17 pgs.

Saudi Arabian Second Substantive Examination Report dated Dec. 9, 2024, pertaining to SA Patent Application No. 523441106, 7 pgs.

International Search Report and Written Opinion dated Nov. 29, 2022, pertaining to Int'l Patent Application No. PCT/US2022/075061.

International Search Report and Written Opinion dated Nov. 30, 2022, pertaining to Int'l Patent Application No. PCT/US2022/041037.

Kuwait Examination Report dated Apr. 28, 2025, pertaining to KW Patent Application No. KW/P/2023/003388, 6 pgs.

Kuwait Office Action dated Apr. 13, 2025, pertaining to KW Patent Application No. KW/P/2023/003387, 7 pgs.

Chinese Office Action dated Jun. 20, 2025, pertaining to CN Patent Application No. 2021800824156, 14 pgs.

Chinese Office Action dated Oct. 29, 2025, pertaining to CN Patent Application No. 202180082415.6, 8 pgs.

Brazilian Technical Report dated Feb. 5, 2026, pertaining to BR Patent Application No. BR112023011215.0, 8 pgs.

Brazilian Technical Report dated Feb. 18, 2026, pertaining to BR Patent Application No. BR112023011226.5, 8 pgs.

Brazilian Technical Report dated Feb. 26, 2026, pertaining to BR Patent Application No. BR112023011402.0, 8 pgs.

Chinese Office Action dated Mar. 18, 2026, pertaining to CN Patent Application No. 202180082620.2, 13 pgs.

US Non-Final Office Action dated Mar. 25, 2026, pertaining to U.S. Appl. No. 18/681,733 6 pgs.

Chinese Office Action dated Apr. 4, 2026, pertaining to CN Patent Application No. 202280054164.5, 15 pgs.

US Non-Final Office Action dated Apr. 20, 2026, pertaining to U.S. Appl. No. 18/681,732, 6 pgs.

(56) References Cited

OTHER PUBLICATIONS

US Non-Final Office Action dated Apr. 29, 2026, pertaining to U.S. Appl. No. 18/257,328, 10 pgs.
US Notice of Allowance dated May 6, 2026, pertaining to U.S. Appl. No. 18/257,361, 9 pgs.
US Office Action dated Apr. 29, 2026, pertaining to U.S. Appl. No. 18/257,364, 8 pgs.
Japanese Notice of Reasons for Refusal dated Jan. 28, 2026, pertaining to JP Patent Application No. 2023-535021, 6 pgs.
Korean Office Action dated Nov. 27, 2025, pertaining to KR Patent Application No. 10-2023-7023305, 7 pgs.
Chinese Office Action dated Dec. 19, 2025, pertaining to CN Patent Application No. 202180081720.3, 10 pgs.
Chinese Office Action dated Dec. 24, 2025, pertaining to CN Patent Application No. 202280054178.7, 15 pgs.
Japanese Office Action dated Apr. 22, 2026, pertaining to JP Patent Application No. 2024-509478, 8 pgs.
Japanese Office Action dated May 25, 2026, pertaining to JP Patent Application No. 2024-509477, 6 pgs.
Chinese Office Action dated Jun. 3, 2026, pertaining to CN Patent Application No. 202180081370.0, 11 pgs.
US Non-Final Office Action dated Jun. 4, 2026, pertaining to U.S. Appl. No. 18/257,364, 11 pgs.

* cited by examiner

SYSTEMS AND METHODS FOR PRODUCING OLEFINS

CROSS-REFERENCE TO RELATED APPLICATIONS

This application is a National Stage Entry under 35 U.S.C. § 371 of International Patent Application No. PCT/US2021/063293, filed Dec. 14, 2021, which claims the benefit of and priority to U.S. Provisional Patent Application Ser. No. 63/126,095 filed on Dec. 16, 2020, and entitled "Systems and Methods for Producing Olefins," the entire contents of both of which are incorporated by reference in the present disclosure.

TECHNICAL FIELD

Embodiments described herein generally relate to chemical processing and, more specifically, to methods and systems for catalytic chemical conversion.

BACKGROUND

Light olefins may be utilized as base materials to produce many types of goods and materials. For example, ethylene may be utilized to manufacture polyethylene, ethylene chloride, or ethylene oxides. Such products may be utilized in product packaging, construction, textiles, etc. Thus, there is an industry demand for light olefins, such as ethylene, propylene, and butene. Light olefins may be produced by different reaction processes depending on the given chemical feed stream, which may be a product stream from a crude oil refining operation. Many light olefins may be produced through processes employing particulate solids, such as solid particulate catalysts.

SUMMARY

Some reactor systems for processing hydrocarbon feeds to produce olefins include a reaction vessel positioned directly below a particulate solid separation section where a riser (connecting the reaction vessel to the separation section) extends from the reaction vessel through the bottom of the particulate solid separation section. Such designs may negatively impact the flow of particulate solids through the particulate solid separation section by creating an annular space in the bottom portion of the particulate solid separation section where an outlet cannot be centered at the bottom of the particulate solid separation section. Additionally, such designs may result in a riser that is longer than necessary, which may allow for undesirable secondary reactions that may reduce the yield of light olefins to occur. Furthermore, such designs may result in more costly process equipment, as an internal riser may require high grade materials and the bottom of the separation section may have a larger diameter to account for the volume occupied by an internal riser. There is a need for improved methods for producing olefins and for improved system components for producing olefins.

Presently disclosed are methods and systems for producing olefins that that may address the problems identified with previous designs. In one or more embodiments, the riser does not enter the particulate solid separation section through the bottom of the particulate solid separation section, resulting in improved flow characteristics of particulate solids exiting the particulate solid separation section. Additionally, in embodiments disclosed herein, the riser may have a shorter length compared to a riser that enters through the bottom of the particulate solid separation section. This may lead to reduced residence time during which secondary reactions that reduce the yield of light olefins may occur.

According to one or more embodiments disclosed herein, olefins may be produced by a method comprising contacting a hydrocarbon feed stream with a particulate solid in a reaction vessel. Contacting the hydrocarbon feed stream with the particulate solid may react the hydrocarbon feed stream to form an olefin-containing product stream. The reaction vessel may be connected to a riser, and the reaction vessel may have a maximum cross sectional area that is at least 3 times the maximum cross sectional area of the riser. The method may further comprise passing the particulate solid through the riser. The riser may extend through a riser port of an outer shell of a particulate solid separation section such that the riser may comprise an interior riser segment positioned in an interior region of the particulate solid separation section and an exterior riser segment positioned outside of an outer shell of the particulate solid separation section. The particulate solid separation section may comprise at least an outer shell defining an interior region of the particulate solid separation section. The outer shell may comprise a gas outlet port, a riser port, and a particulate solid outlet port. The outer shell may house a gas/solids separation device and a solid particulate collection area in the interior region of the particulate solid separation section. The riser port may be positioned on a sidewall of the outer shell such that it is not located on a central vertical axis of the particulate solid separation section. The method may further comprise separating the particulate solid from the olefin-containing product stream in the gas/solids separation device and passing the particulate solids, separated from the olefin-containing product stream, to the solid particulate collection area located proximate the central vertical axis of the particulate solid separation section.

It is to be understood that both the foregoing brief summary and the following detailed description present embodiments of the technology, and are intended to provide an overview or framework for understanding the nature and character of the technology as it is claimed. The accompanying drawings are included to provide a further understanding of the technology, and are incorporated into and constitute a part of this specification. The drawings illustrate various embodiments and, together with the description, serve to explain the principles and operations of the technology. Additionally, the drawings and descriptions are meant to be merely illustrative, and are not intended to limit the scope of the claims in any manner.

Additional features and advantages of the technology disclosed herein will be set forth in the detailed description that follows, and in part will be readily apparent to those skilled in the art from that description or recognized by practicing the technology as described herein, including the detailed description that follows, the claims, as well as the appended drawings.

BRIEF DESCRIPTION OF THE DRAWINGS

The following detailed description of specific embodiments of the present disclosure can be best understood when read in conjunction with the following drawings, where like structure is indicated with like reference numerals and in which.

Figure 1:
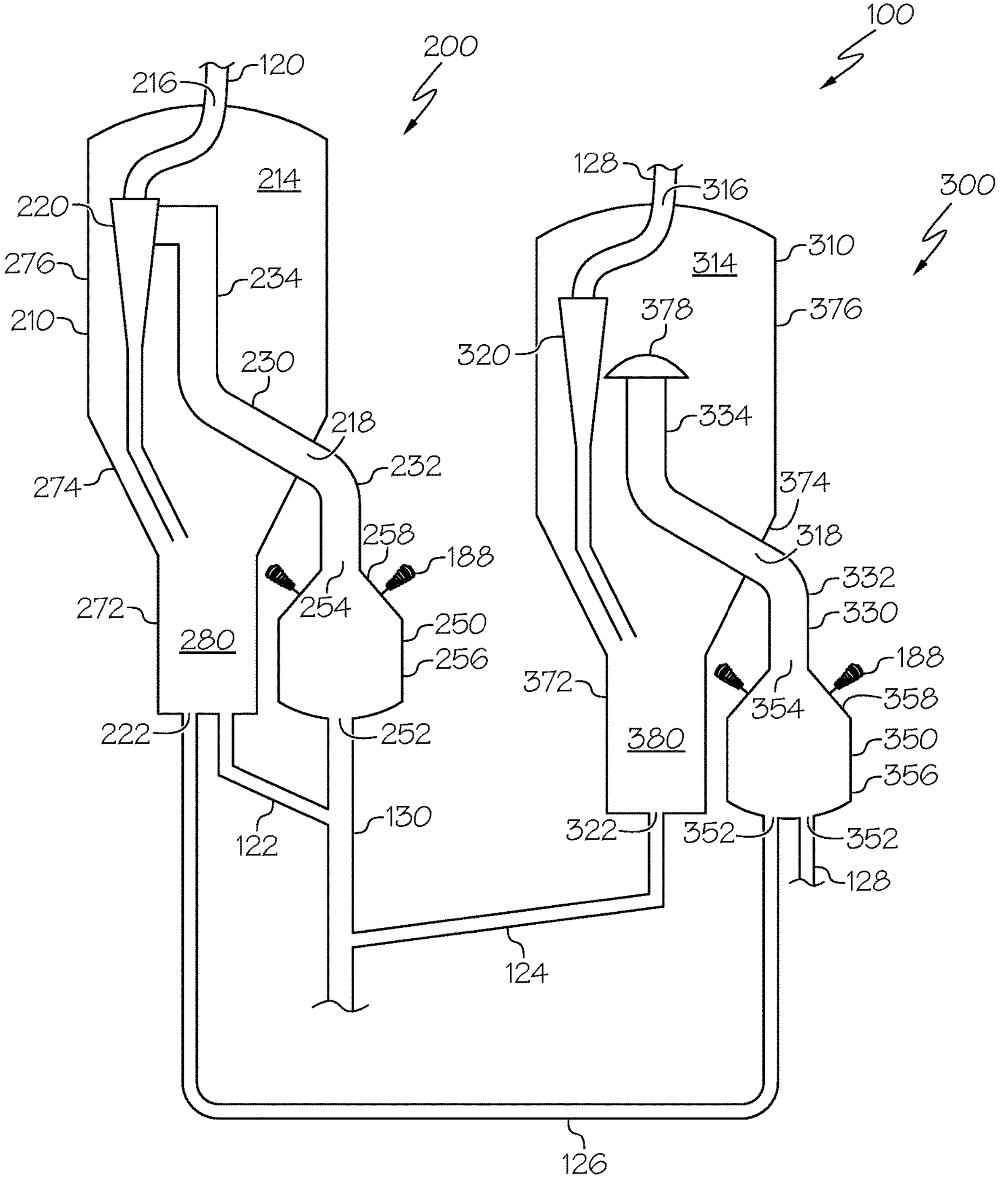
FIG. 1 schematically depicts a reactor system comprising a reactor section and a regenerator section, according to one or more embodiments disclosed herein.

It should be understood that the drawings are schematic in nature, and do not include some components of a fluid catalytic reactor system commonly employed in the art, such as, without limitation, temperature transmitters, pressure transmitters, flow meters, pumps, valves, and the like. It would be known that these components are within the spirit and scope of the present embodiments disclosed. However, operational components, such as those described in the present disclosure, may be added to the embodiments described in this disclosure.

Reference will now be made in greater detail to various embodiments, some embodiments of which are illustrated in the accompanying drawings. Whenever possible, the same reference numerals will be used throughout the drawings to refer to the same or similar parts.

DETAILED DESCRIPTION

Methods for producing olefins from hydrocarbon feed streams are disclosed herein. Such methods utilize systems which have particular features, such as a particular orientation of system parts. For example, in one or more embodiments described herein, the reaction vessel is not directly below the separation section. One particular embodiment, which is disclosed in detail herein, is depicted in FIG. 1. However, it should be understood that the principles disclosed and taught herein may be applicable to other systems which utilize different system components oriented in different ways, or different reaction schemes utilizing various catalyst compositions.

Now referring to FIG. 1, as may be understood with reference to the forgoing figures and description, feed chemical may be reacted by contact with the particulate solid, such as a catalyst, in a reactor section 200. The particulate solid may be separated from the reaction products in the reactor section 200 and passed to the regeneration section 300. In the regeneration section 300, the particulate solid may be regenerated. Such regenerated particulate solid may be passed back to the reactor section 200 for subsequent cycles of the reaction.

While some embodiments are described herein in the context of a reactor system 100, it should be understood that the methods and systems described herein may operate without the use of the regeneration section 300, or with alternative means for regenerating particulate solids. As such, it should not be construed that the regeneration section 300 is required or essential in all embodiments of the presently disclosed methods and systems.

In non-limiting examples, the reactor system 100 described herein may be utilized to produce light olefins from hydrocarbon feed streams. Light olefins may be produced from a variety of hydrocarbon feed streams by utilizing different reaction mechanisms. For example, light olefins may be produced by at least dehydrogenation reactions, cracking reactions, dehydration reactions, and methanol-to-olefin reactions. These reaction types may utilize different feed streams and different particulate solids to produce light olefins. It should be understood that when "catalysts" are referred to herein, they may equally refer to the particulate solid referenced with respect to the system of FIG. 1.

According to one or more embodiments, the reaction may be a dehydrogenation reaction. According to such embodiments, the hydrocarbon feed stream may comprise one or more of ethyl benzene, ethane, propane, n-butane, and i-butane. In one or more embodiments, the hydrocarbon feed stream may comprise at least 50 wt. %, at least 60 wt. %, at least 70 wt. %, at least 80 wt. %, at least 90 wt. %, at least 95 wt. % or even at least 99 wt. % of ethyl benzene. In one or more embodiments, the hydrocarbon feed stream may comprise at least 50 wt. %, at least 60 wt. %, at least 70 wt. %, at least 80 wt. %, at least 90 wt. %, at least 95 wt. % or even at least 99 wt. % of ethane. In additional embodiments, the hydrocarbon feed stream may comprise at least 50 wt. %, at least 60 wt. %, at least 70 wt. %, at least 80 wt. %, at least 90 wt. %, at least 95 wt. % or even at least 99 wt. % of propane. In additional embodiments, the hydrocarbon feed stream may comprise at least 50 wt. %, at least 60 wt. %, at least 70 wt. %, at least 80 wt. %, at least 90 wt. %, at least 95 wt. % or even at least 99 wt. % of n-butane. In additional embodiments, the hydrocarbon feed stream may comprise at least 50 wt. %, at least 60 wt. %, at least 70 wt. %, at least 80 wt. %, at least 90 wt. %, at least 95 wt. % or even at least 99 wt. % of i-butane. In additional embodiments, the hydrocarbon feed stream may comprise at least 50 wt. %, at least 60 wt. %, at least 70 wt. %, at least 80 wt. %, at least 90 wt. %, at least 95 wt. % or even at least 99 wt. % of the sum of ethane, propane, n-butane, and i-butane.

In one or more embodiments, the dehydrogenation reaction may utilize gallium and/or platinum particulate solids as a catalyst. In such embodiments, the particulate solids may comprise a gallium and/or platinum catalyst. As described herein, a gallium and/or platinum catalyst comprises gallium, platinum, or both. The gallium and/or platinum catalyst may be carried by an alumina or alumina silica support, and may optionally comprise potassium. Such gallium and/or platinum catalysts are disclosed in U.S. Pat. No. 8,669,406, which is incorporated herein by reference in its entirety. However, it should be understood that other suitable catalysts may be utilized to perform the dehydrogenation reaction.

In one or more embodiments, the reaction mechanism may be dehydrogenation followed by combustion (in the same chamber). In such embodiments, a dehydrogenation reaction may produce hydrogen as a byproduct, and an oxygen carrier material may contact the hydrogen and promote combustion of the hydrogen, forming water. Examples of such reaction mechanisms, which are contemplated as possible reactions mechanisms for the systems and methods described herein, are disclosed in WO 2020/046978, the teachings of which are incorporated by reference in their entirety herein.

According to one or more embodiments, the reaction may be a cracking reaction. According to such embodiments, the hydrocarbon feed stream may comprise one or more of naphtha, n-butane, or i-butane. According to one or more embodiments, the hydrocarbon feed stream may comprise at least 50 wt. %, at least 60 wt. %, at least 70 wt. %, at least 80 wt. %, at least 90 wt. %, at least 95 wt. % or even at least 99 wt. % of naphtha. In additional embodiments, the hydrocarbon feed stream may comprise at least 50 wt. %, at least 60 wt. %, at least 70 wt. %, at least 80 wt. %, at least 90 wt. %, at least 95 wt. % or even at least 99 wt. % of n-butane. In additional embodiments, the hydrocarbon feed stream may comprise at least 50 wt. %, at least 60 wt. %, at least 70 wt. %, at least 80 wt. %, at least 90 wt. %, at least 95 wt. % or even at least 99 wt. % of i-butane. In additional embodiments, the hydrocarbon feed stream may comprise at least 50 wt. %, at least 60 wt. %, at least 70 wt. %, at least 80 wt. %, at least 90 wt. %, at least 95 wt. % or even at least 99 wt. % of the sum of naphtha, n-butane, and i-butane.

In one or more embodiments, the cracking reaction may utilize one or more zeolites as a catalyst. In such embodiments, the particulate solids may comprise one or more zeolites. In some embodiments, the one or more zeolites utilized in the cracking reaction may comprise a ZSM-5 zeolite. However, it should be understood that other suitable catalysts may be utilized to perform the cracking reaction. For example, suitable catalysts that are commercially available may include Intercat Super Z Excel or Intercat Super Z Exceed. In additional embodiments, the cracking catalyst may comprise, in addition to a catalytically active material, platinum. For example, the cracking catalyst may include from 0.001 wt. % to 0.05 wt. % of platinum. The platinum may be sprayed on as platinum nitrate and calcined at an elevated temperature, such as around 700° C. Without being bound by theory, it is believed that the addition of platinum to the catalyst may allow for easier combustion of supplemental fuels, such as methane.

According to one or more embodiments, the reaction may be a dehydration reaction. According to such embodiments, the hydrocarbon feed stream may comprise one or more of ethanol, propanol, or butanol. According to one or more embodiments, the hydrocarbon feed stream may comprise at least 50 wt. %, at least 60 wt. %, at least 70 wt. %, at least 80 wt. %, at least 90 wt. %, at least 95 wt. % or even at least 99 wt. % of ethanol. In additional embodiments, the hydrocarbon feed stream may comprise at least 50 wt. %, at least 60 wt. %, at least 70 wt. %, at least 80 wt. %, at least 90 wt. %, at least 95 wt. % or even at least 99 wt. % of propanol. In additional embodiments, the hydrocarbon feed stream may comprise at least 50 wt. %, at least 60 wt. %, at least 70 wt. %, at least 80 wt. %, at least 90 wt. %, at least 95 wt. % or even at least 99 wt. % of butanol. In additional embodiments, the hydrocarbon feed stream or may comprise at least 50 wt. %, at least 60 wt. %, at least 70 wt. %, at least 80 wt. %, at least 90 wt. %, at least 95 wt. % or even at least 99 wt. % of the sum of ethanol, propanol, and butanol.

In one or more embodiments, the dehydration reaction may utilize one or more acid catalysts. In such embodiments, the particulate solids may comprise one or more acid catalysts. In some embodiments, the one or more acid catalysts utilized in the dehydration reaction may comprise a zeolite (such as ZSM-5 zeolite), alumina, amorphous aluminosilicate, acid clay, or combinations thereof. For example, commercially available alumina catalysts which may be suitable, according to one or more embodiments, include SynDol (available from Scientific Design Company), V200 (available from UOP), or P200 (available from Sasol). Commercially available zeolite catalysts which may be suitable include CBV 8014, CBV 28014 (each available from Zeolyst). Commercially available amorphous aluminosilicate catalysts which may be suitable include silica-alumina catalyst support, grade 135 (available from Sigma Aldrich). However, it should be understood that other suitable catalysts may be utilized to perform the dehydration reaction.

According to one or more embodiments, the reaction may be a methanol-to-olefin reaction. According to such embodiments, the hydrocarbon feed stream may comprise methanol. According to one or more embodiments, the hydrocarbon feed stream may comprise at least 50 wt. %, at least 60 wt. %, at least 70 wt. %, at least 80 wt. %, at least 90 wt. %, at least 95 wt. % or even at least 99 wt. % of methanol.

In one or more embodiments, the methanol-to-olefin reaction may utilize one or more zeolites as a catalyst. In such embodiments, the particulate solids may comprise one or more zeolites. In some embodiments, the one or more zeolites utilized in the methanol-to-olefin reaction may comprise a one or more of a ZSM-5 zeolite or a SAPO-34 zeolite. However, it should be understood that other suitable catalysts may be utilized to perform the methanol-to-olefin reaction.

In one or more embodiments, the operating of chemical process may include passing the product stream out of the reactor. The product stream may comprise light olefins or alkyl aromatic olefins, such as styrene. As described herein, "light olefins" refers to one or more of ethylene, propylene, or butene. As described herein, butene many include any isomer of butene, such as $\alpha$-butylene, cis-$\beta$-butylene, trans-$\beta$-butylene, and isobutylene. In one embodiment, the product stream may comprise at least 50 wt. % light olefins. For example, the product stream may comprise at least 60 wt. % light olefins, at least 70 wt. % light olefins, at least 80 wt. % light olefins, at least 90 wt. % light olefins, at least 95 wt. % light olefins, or even at least 99 wt. % light olefins.

Still referring to FIG. 1, the reactor system 100 generally comprises multiple system components, such as a reactor section 200 and a regeneration section 300. As used herein in the context of FIG. 1, a reactor section 200 generally refers to the portion of a reactor system 100 in which the major process reaction takes place, and the particulate solids are separated from the olefin-containing product stream of the reaction. In one or more embodiments, the particulate solids may be spent, meaning that they are at least partially deactivated. Also, as used herein, a regeneration section 300 generally refers to the portion of a fluid catalytic reactor system where the particulate solids are regenerated, such as through combustion, and the regenerated particulate solids are separated from the other process material, such as evolved gasses from the combusted material previously on the spent particulate solids or from supplemental fuel. The reactor section 200 generally includes a reaction vessel 250, a riser 230 including an exterior riser segment 232 and an interior riser segment 234, and a particulate solid separation section 210. The regeneration section 300 generally includes a particulate solid treatment vessel 350, a riser 330 including an exterior riser segment 332 and an interior riser segment 334, and a particulate solid separation section 310. Generally, the particulate solid separation section 210 may be in fluid communication with the particulate solid treatment vessel 350, for example, by standpipe 126, and the particulate solid separation section 310 may be in fluid communication with the reaction vessel 250, for example, by standpipe 124 and transport riser 130.

Generally, the reactor system 100 may be operated by feeding a hydrocarbon feed and fluidized particulate solids into the reaction vessel 250, and reacting the hydrocarbon feed by contact with fluidized particulate solids to produce an olefin-containing product in the reaction vessel 250 of the reactor section 200. The olefin-containing product and the particulate solids may be passed out of the reaction vessel 250 and through the riser 230 to a gas/solids separation device 220 in the particulate solid separation section 210, where the particulate solids may be separated from the olefin-containing product. The particulate solids may then be transported out of the particulate solid separation section 210 to the particulate solid treatment vessel 350. In the particulate solid treatment vessel 350, the particulate solids may be regenerated by chemical processes. For example, the spent particulate solids may be regenerated by one or more of oxidizing the particulate solid by contact with an oxygen containing gas, combusting coke present on the particulate solids, and combusting a supplemental fuel to heat the particulate solid. The particulate solids may then be passed out of the particulate solid treatment vessel 350 and through the riser 330 to a riser termination device 378, where the gas and particulate solids from the riser 330 are partially separated. The gas and remaining particulate solids from the riser 330 are transported to gas/solids separation device 320 in the particulate solid separation section 310 where the remaining particulate solids are separated from the gasses from the regeneration reaction. The particulate solids, separated from the gasses, may be passed to a solid particulate collection area 380. The separated particulate solids are then passed from the solid particulate collection area 380 to the reaction vessel 250, where they are further utilized. Thus, the particulate solids may cycle between the reactor section 200 and the regeneration section 300.

In one or more embodiments, the reactor system 100 may include either a reactor section 200 or a regeneration section 300, and not both. In further embodiments, the reactor system 100 may include a single regeneration section 300 and multiple reactor sections 200.

Additionally, as described herein, the structural features of the reactor section 200 and regeneration section 300 may be similar or identical in some respects. For example, each of the reactor section 200 and regeneration section 300 include a reaction vessel (i.e., reaction vessel 250 of the reactor section 200 and particulate solid treatment vessel 350 of the regeneration section 300), a riser (i.e., riser 230 of the reactor section 200 and riser 330 of the regeneration section 300), and a particulate solid separation section (i.e., particulate solid separation section 210 of the reactor section 200 and particulate solid separation section 310 of the regeneration section 300). It should be appreciated that since many of the structural features of the reactor section 200 and the regeneration section 300 may be similar or identical in some respects, similar or identical portions of the reactor section 200 and the regeneration section 300 have been provided reference numbers throughout this disclosure with the same final two digits, and disclosures related to one portion of the reactor section 200 may be applicable to the similar or identical portion of the regeneration section 300, and vice versa.

Figure 2:
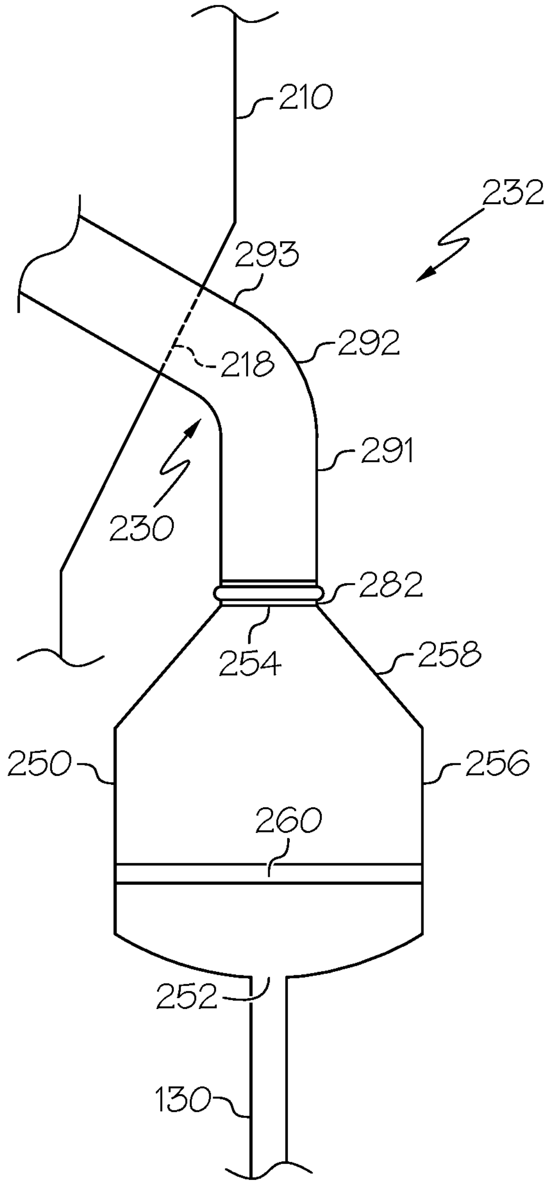
FIG. 2 schematically depicts a reaction vessel and exterior riser segment, according to one or more embodiments disclosed herein.

As depicted in FIGS. 1 and 2, the reaction vessel 250 may include a reaction vessel particulate solid inlet port 252 defining the connection of transport riser 130 to the reaction vessel 250. The reaction vessel 250 may additionally include a reaction vessel outlet port 254 in fluid communication with, or directly connected to, the exterior riser segment 232 of the riser 230. As described herein, a "reaction vessel" refers to a drum, barrel, vat, or other container suitable for a given chemical reaction. A reaction vessel may be generally cylindrical in shape (i.e., having a substantially circular diameter), or may alternately be non-cylindrically shaped, such as prism shaped with cross-sectional shaped of triangles, rectangles, pentagons, hexagons, octagons, ovals, or other polygons or curved closed shapes, or combinations thereof. Reaction vessels, as used throughout this disclosure, may generally include a metallic frame, and may additionally include refractory linings or other materials utilized to protect the metallic frame and/or control process conditions.

Generally, "inlet ports" and "outlet ports" of any system unit of the fluid catalytic reactor system 100 described herein refer to openings, holes, channels, apertures, gaps, or other like mechanical features in the system unit. For example, inlet ports allow for the entrance of materials to the particular system unit and outlet ports allow for the exit of materials from the particular system unit. Generally, an outlet port or inlet port will define the area of a system unit of the fluid catalytic reactor system 100 to which a pipe, conduit, tube, hose, transport line, or like mechanical feature is attached, or to a portion of the system unit to which another system unit is directly attached. While inlet ports and outlet ports may sometimes be described herein functionally in operation, they may have similar or identical physical characteristics, and their respective functions in an operational system should not be construed as limiting on their physical structures. Other ports, such as the riser port 218, may comprise an opening in the given system unit where other system units are directly attached, such as where the riser 230 extends into the particulate solid separation section 210 at the riser port 218.

The reaction vessel 250 may be connected to a transport riser 130, which in operation, may provide regenerated particulate solids and chemical feed to the reactor section 200. As displayed in FIG. 2, the regenerated particulate solids and the chemical feed may be mixed with a distributor 260 housed in the reaction vessel 250. Referring again to FIG. 1, the particulate solids entering the reaction vessel 250 via transport riser 130 may be passed through standpipe 124 to a transport riser 130, thus arriving from the regeneration section 300. In some embodiments, particulate solids may come directly from the particulate solid separation section 210 via standpipe 122 and into a transport riser 130, where they enter the reaction vessel 250. These particulate solids may be slightly deactivated, but may still, in some embodiments, be suitable for use in the reaction vessel 250.

As depicted in FIGS. 1 and 2, the reaction vessel 250 may be directly connected to the exterior riser segment 232. In one embodiment, the reaction vessel 250 may include a reaction vessel body section 256 and a reaction vessel transition section 258 positioned between the reaction vessel body section 256 and the exterior riser segment 232. The reaction vessel body section 256 may generally comprise a greater diameter than the reaction vessel transition section 258, and the reaction vessel transition section 258 may be tapered from the size of the diameter of the reaction vessel body section 256 to the size of the diameter of the riser 230, such that the reaction vessel transition section 258 projects inwardly from the reaction vessel body section 256 to the exterior riser segment 232. It should be understood that, as used herein, the diameter of a portion of a system unit refers to its general width, as shown in the horizontal direction in FIG. 1.

Additionally, the reaction vessel body section 256 may generally comprise a height, where the height of the reaction vessel body section 256 is measured from the particulate solid inlet port 152 to the reaction vessel transition section 258. In one or more embodiments, the diameter of the reaction vessel body section 256 may be greater than the height of the reaction vessel body section 256. In one or more embodiments, the ratio of the diameter to the height of the reaction vessel body section 256 may be from 5:1 to 1:5. For example, the ratio of the diameter to the height of the particulate solid treatment vessel body section 356 may be from 5:1 to 1:5, from 4:1 to 1:5, from 3:1 to 1:5, from 2:1 to 1:5, from 1:1 to 1:5, from 1:2 to 1:5, from 1:3 to 1:5, from 1:4 to 1:5, from 5:1 to 1:4, from 5:1 to 1:3, from 5:1 to 1:2, from 5:1 to 1:1, from 5:1 to 2:1, from 5:1 to 3:1, from 5:1 to 4:1, or any combination or sub-combination of these ranges.

In one or more embodiments, the reaction vessel 250 may have a maximum cross sectional area that is at least 3 times the maximum cross sectional area of the riser 230. For example, the reaction vessel 250 may have a maximum cross sectional area that is at least 3, at least 4, at least 5, at least 6, at least 7, at least 8, at least 9, or even at least 10 times the maximum cross sectional area of the riser 230. As described herein, unless otherwise explicitly stated, the "cross sectional area" refers to the area of the cross section of a portion of a system component in a plane substantially orthogonal to the direction of general flow of reactants and/or products.

In one or more embodiments, based on the shape, size, and other processing conditions such as temperature and pressure in the reaction vessel 250 and the riser 230, the reaction vessel 250 may operate in a manner that is or approaches isothermal, such as in a fast fluidized, turbulent, or bubbling bed reactor, while the riser 230 may operate in more of a plug flow manner, such as in a dilute phase riser reactor. For example, the reaction vessel 250 may operate as a fast fluidized, turbulent, or bubbling bed reactor and the riser 230 may operate as a dilute phase riser reactor, with the result that the average catalyst and gas flow moves concurrently upward. As the term is used herein, "average flow" refers to the net flow, i.e., the total upward flow minus the retrograde or reverse flow, as is typical of the behavior of fluidized particles in general. As described herein, a "fast fluidized" reactor may refer to a reactor utilizing a fluidization regime wherein the superficial velocity of the gas phase is greater than the choking velocity and may be semi-dense in operation. As described herein, a "turbulent" reactor may refer to a fluidization regime where the superficial velocity of less than the choking velocity and is more dense than the fast fluidized regime. As described herein, a "bubbling bed" reactor may refer to a fluidization regime wherein well-defined bubbles in a highly dense bed are present in two distinct phases. The "choking velocity" refers to the minimum velocity required to maintain solids in the dilute-phase mode in a vertical conveying line. As described herein, a "dilute phase riser" may refer to a riser reactor operating at transport velocity, where the gas and catalyst have about the same velocity in a dilute phase.

In one or more embodiments, the pressure in the reaction vessel 250 may range from 6.0 to 100 pounds per square inch absolute (psia, from about 41.4 kilopascals, kPa, to about 689.4 kPa), but in some embodiments, a narrower selected range, such as from 15.0 psia to 35.0 psia, (from about 103.4 kPa to about 241.3 kPa), may be employed. For example, the pressure may be from 15.0 psia to 30.0 psia (from about 103.4 kPa to about 206.8 kPa), from 17.0 psia to 28.0 psia (from about 117.2 kPa to about 193.1 kPa), or from 19.0 psia to 25.0 psia (from about 131.0 kPa to about 172.4 kPa). Unit conversions from standard (non-SI) to metric (SI) expressions herein include "about" to indicate rounding that may be present in the metric (SI) expressions as a result of conversions.

In additional embodiments, the weight hourly space velocity (WHSV) for the disclosed process may range from 0.1 pound (lb) to 100 lb of chemical feed per hour (h) per lb of catalyst in the reactor (lb feed/h/lb catalyst). For example, where a reactor comprises a reaction vessel 250 that operates as a fast fluidized, turbulent, or bubbling bed reactor and a riser 230 that operates as a riser reactor, the superficial gas velocity may range therein from 2 feet per second (ft/s, about 0.61 meters per second, m/s) to 80 ft/s (about 24.38 m/s), such as from 2 ft/s (about 0.61 m/s) to 10 ft/s (about 3.05 m/s), in the reaction vessel 250, and from 30 ft/s (about 9.14 m/s) to 70 ft/s (about 21.31 m/s) in the riser 230. In additional embodiments, a reactor configuration that is fully of a riser type may operate at a single high superficial gas velocity, for example, in some embodiments at least 30 ft/s (about 9.15 m/s) throughout.

In additional embodiments, the ratio of catalyst to feed stream in the reaction vessel 250 and riser 230 may range from 5 to 100 on a weight to weight (w/w) basis. In some embodiments, the ratio may range from 10 to 40, such as from 12 to 36, or from 12 to 24.

In additional embodiments, the catalyst flux may be from 1 pound per square foot-second (lb/ft$^2$-s) (about 4.89 kg/m$^2$-s) to 30 lb/ft$^2$-s (to about 146.5 kg/m2-s) in the reaction vessel 250, and from 10 lb/ft$^2$-s (about 48.9 kg/m2-s) to 250 lb/ft$^2$-s (about 1221 kg/m2-s) in the riser 230.

Still referring to FIG. 1, the reactor section 200 may comprise a riser 230, which acts to transport reactants, products, and/or particulate solids from the reaction vessel 250 to the particulate solid separation section 210. In one or more embodiments, the riser 230 may be generally cylindrical in shape (i.e., having a substantially circular cross-sectional shape), or may alternately be non-cylindrically shaped, such as prism shaped with cross-sectional shape of triangles, rectangles, pentagons, hexagons, octagons, ovals, or other polygons or curved closed shapes, or combinations thereof. The riser 230, as used throughout this disclosure, may generally include a metallic frame, and may additionally include refractory linings or other materials utilized to protect the metallic frame and/or control process conditions.

According to some embodiments, the riser 230 may include an exterior riser segment 232 and an interior riser segment 234. As used herein, an "exterior riser segment" refers to the portion of the riser that is outside of the particulate solid separation section, and an "interior riser segment" refers to the portion of the riser that is within the particulate solid separation section. For example, in the embodiment depicted in FIG. 1, the interior riser segment 234 of the reactor section 200 may be positioned within the particulate solid separation section 210, while the exterior riser segment 232 is positioned outside of the particulate solid separation section 210.

Figure 3:
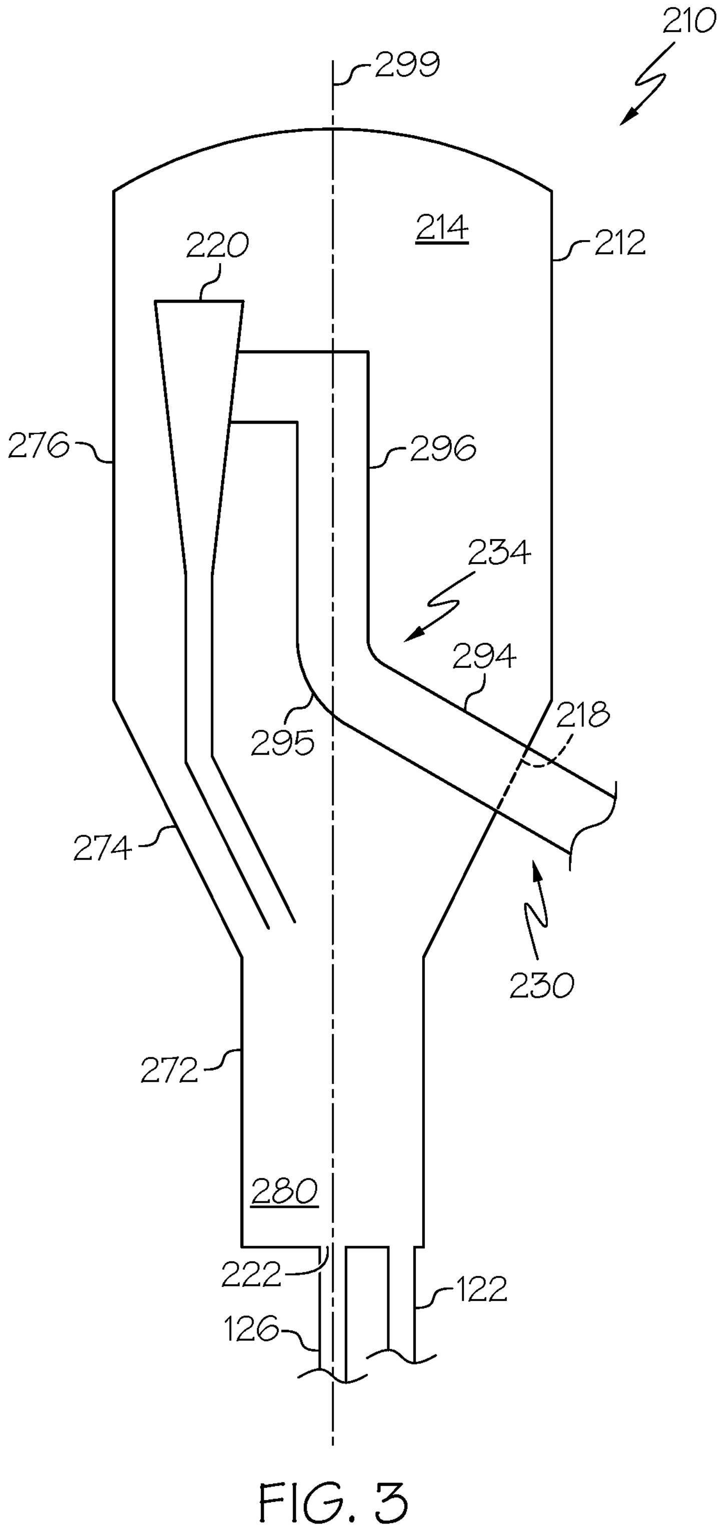
FIG. 3 schematically depicts a particulate solid separation section, according to one or more embodiments disclosed herein.

Referring to FIGS. 1 and 3, the particulate solid separation section 210 may comprise an outer shell 212 where the outer shell 212 may define an interior region 214 of the particulate solid separation section 210. The outer shell 212 may comprise a gas outlet port 216, a riser port 218, and a particulate solid outlet port 222. Furthermore, the outer shell 212 may house a gas/solids separation device 220 and a particulate solid collection area 280 in the interior region 214 of the particulate solid separation section 210.

In one or more embodiments, the outer shell 212 of the particulate solid separation section 210 may define an upper segment 276, a middle segment 274, and a lower segment 272 of the particulate solid separation section 210. Generally, the upper segment 276 may have a substantially constant cross sectional area, such that the cross sectional area does not vary by more than 20% in the upper segment 276. In one or more embodiments, the cross sectional area of the upper segment 276 may be at least three times the maximum cross sectional area of the riser 230. For example, the cross sectional area of the upper segment 276 may be at least 3 times, at least 4 times, at least 5 times, at least 6 times, at least 7 times, at least 8 times, at least 9 times, at least 10 times, at least 12 times, at least 15 times, or even at least 20 times the maximum cross sectional area of the riser 230. In further embodiments, the maximum cross sectional area of the upper segment 276 may be from 5 to 40 times the maximum cross sectional area of the riser 230. For example, the maximum cross sectional area of the upper segment 276 may be from 5 to 40, from 10 to 40, from 15 to 40, from 20 to 40, from 25 to 40, from 30 to 40, from 35 to 40, from 5 to 35, from 5 to 30, from 5 to 25, from 5 to 20, from 5 to 15, or even from 5 to 10 times the maximum cross sectional area of the riser 230.

Additionally, in one or more embodiments, the lower segment 272 of the particulate solid separation section 210 may have a substantially constant cross sectional area, such that the cross sectional area does not vary by more than 20% in the lower segment 272. The cross sectional area of the lower segment 272 may be larger than the maximum cross sectional area of the riser 230 and smaller than the maximum cross sectional area of the upper segment 276. The middle segment 274 may be shaped as a frustum where the cross sectional area of the middle segment 274 is not constant and the cross sectional area of the middle segment 274 transitions from the cross sectional area of the upper segment 276 to the cross sectional area of the lower segment 272 throughout the middle segment 274.

Referring again to FIG. 3, the particulate solid separation section 210 may comprise a central vertical axis 299. The central vertical axis may extend through the top of the particulate solid separation section 210 and the bottom of the particulate solid separation section 210, such that the central vertical axis 299 passes through the upper segment 276, the middle segment 274, and the lower segment 272 of the particulate solid separation section 210. In one or more embodiments, the upper segment 276, the middle segment 274, and the lower segment 272 of the particulate solid separation section 210 may be centered on the central vertical axis 299. For example, in embodiments where the upper segment 276 and the lower segment 272 are substantially cylindrical, the central vertical axis 299 may pass through the midpoint of a diameter of the upper segment 276 and a midpoint of a diameter of the lower segment 272.

As depicted in FIGS. 1 and 3, the interior riser segment 234 of the riser 230 may extend through the riser port 218 of the particulate solid separation section 210. The riser port 218 may be any opening in the outer shell 212 of the particulate solid separation section 210 through which at least the interior riser segment 234 of the riser 230 protrudes into the interior region 214 of the particulate solid separation section 210. In one or more embodiments, the riser port 218 is not located on the central vertical axis 299 of the particulate solid separation section 210. In such embodiments, the riser port 218 may be located on a sidewall of the outer shell 212 such that the riser port 218 is neither located on the central vertical axis 299 nor oriented so that the riser 230 extends into the particulate solid separation section 210 in a direction substantially parallel to the central vertical axis 299.

In one or more embodiments, the interior riser segment 234 enters the particulate solid separation section 210 in the middle segment 274 of the particulate solid separation section 210. In such embodiments, the interior riser segment 234 passes through at least a portion of the middle segment 274 and through at least a portion of the upper segment 276. In such embodiments, the interior riser segment 234 does not pass through the lower segment 272 of the particulate solid separation section 210. In further embodiments, the interior riser segment 234 may enter the particulate solid separation section 210 in the upper segment 276 and the interior riser segment 234 may pass through at least a portion of the upper segment 276. In such embodiments, the interior riser segment 234 does not pass through the lower segment 272 or the middle segment 274.

Referring now to FIG. 3, the interior riser segment 234 may comprise a vertical portion 296, a non-vertical portion 294, and a non-linear portion 295. As described herein, a "non-linear portion" may refer to a portion of a riser segment comprising a curve or a mitered junction. The non-linear portion 295 may be positioned between the vertical portion 296 and the non-vertical portion 294 and may connect the vertical portion 296 and the non-vertical portion 294. Additionally, the non-vertical portion 294 of the interior riser segment 234 may be proximate to the riser port 218. In one or more embodiments, the non-vertical portion 294 of the interior riser segment 234 may be adjacent or directly connected to the riser port 218. As such, the riser 230 may extend through the riser port 218 in a non-vertical direction.

Referring again to FIG. 2, the exterior riser segment 232 may comprise a vertical portion 291, a non-vertical portion 293, and a non-linear portion 292. The non-linear portion 292 may be positioned between the vertical portion 291 and the non-vertical portion 293 and may connect the vertical portion 291 and the non-vertical portion 293. The non-vertical portion 293 of the exterior riser segment 232 may be proximate to the riser port 218. In one or more embodiments, the non-vertical portion 293 of the exterior riser segment 232 may be adjacent or directly connected to the riser port 218. Furthermore, the vertical portion 291 of the exterior riser segment 232 may be proximate to the reaction vessel 250. In such embodiments, an expansion joint 282, described in further detail herein, may be positioned between the vertical portion 291 of the exterior riser segment 232 and the reaction vessel 250.

In one or more embodiments, the riser 230 may extend through the riser port 218 in a diagonal direction where the diagonal direction is 15 to 75 degrees from vertical. For example, the diagonal direction may be from 15 to 75 degrees from vertical, from 20 to 75 degrees from vertical, from 25 to 75 degrees from vertical, from 30 to 75 degrees from vertical, from 35 to 75 degrees from vertical, from 40 to 75 degrees from vertical, from 45 to 75 degrees from vertical, from 50 to 75 degrees from vertical, from 55 to 75 degrees from vertical, from 60 to 75 degrees from vertical, from 65 to 75 degrees from vertical, from 70 to 75 degrees from vertical, from 15 to 70 degrees from vertical, from 15 to 65 degrees from vertical, from 15 to 60 degrees from vertical, from 15 to 55 degrees from vertical, from 15 to 50 degrees from vertical, from 15 to 45 degrees from vertical, from 15 to 40 degrees from vertical, from 15 to 35 degrees from vertical, from 15 to 30 degrees from vertical, from 15 to 25 degrees from vertical, from 15 to 20 degrees from vertical, or any combination or sub-combination of these ranges. In one or more alternative embodiments, the riser 230 may pass through the riser port 218 is a substantially horizontal direction. As described herein, a "substantially horizontal" direction may be within 15 degrees of horizontal, within 10 degrees of horizontal, or even within 5 degrees of horizontal.

Without wishing to be bound by theory, it is believed that when the riser port 218 is not located on the central vertical axis 299 and the riser 230 enters the particulate solid separation section 210 in a non-vertical manner, the reaction vessel 250 may be located closer to the gas/solids separation device 220. As such, gasses and particulate solids would travel a shorter distance in the riser 230, reducing the opportunity for secondary reactions to occur within the riser 230. Such secondary reactions may be undesirable as they may lead to a decreased yield of light olefins.

Referring again to FIG. 3, in the upper segment 276 of the particulate solid separation section 210, the interior riser segment 234 may be in fluid communication with the gas/solids separation device 220. For example, the vertical portion 296 of the interior riser segment 234 may be directly connected to the gas/solids separation device 220. The gas/solids separation device 220 may be any mechanical or chemical separation device that may be operable to separate particulate solids from gas or liquid phases, such as a cyclone or a plurality of cyclones.

According to one or more embodiments, the gas/solids separation device 220 may be a cyclonic separation system, which may include two or more stages of cyclonic separation. In embodiments where the gas/solids separation device 220 comprises more than one cyclonic separation stages, the first separation device into which the fluidized stream enters is referred to a primary cyclonic separation device. The fluidized effluent from the primary cyclonic separation device may enter into a secondary cyclonic separation device for further separation. Primary cyclonic separation devices may include, for example, primary cyclones, and systems commercially available under the names VSS (commercially available from UOP), LD2 (commercially available from Stone and Webster), and RS2 (commercially available from Stone and Webster). Primary cyclones are described, for example, in U.S. Pat. Nos. 4,579,716; 5,190,650; and 5,275,641, which are each incorporated by reference in their entirety herein. In some separation systems utilizing primary cyclones as the primary cyclonic separation device, one or more set of additional cyclones, e.g. secondary cyclones and tertiary cyclones, are employed for further separation of the particulate solids from the product gas. It should be understood that any primary cyclonic separation device may be used in embodiments disclosed herein.

The particulate solids may move upward through the riser 230 from the reaction vessel 250 and into the gas/solids separation device 220. The gas/solids separation device 220 may be operable to deposit separated particulate solids into the bottom of the upper segment 276 or into the middle segment 274 or lower segment 272 of the particulate solid separation section 210. The separated vapors may be removed from the fluid catalytic reactor system 100 via a pipe 120 at a gas outlet port 216 of the particulate solid separation section 210.

Referring now to FIGS. 1 and 3, the lower segment 272 of the particulate solid separation section 210 may comprise a particulate solid collection area 280. In one or more embodiments, the particulate solid collection area 280 may allow for accumulation of particulate solids within the particulate solid separation section 210. The particulate solid collection area 280 may comprise a stripping section. The stripping section may be utilized to remove product vapors from the particulate solids prior to sending them to the regeneration section 300. As product vapors transported to the regeneration section 300 will be combusted, it is desirable to remove those product vapors with the stripper, which utilizes less expensive gases than product gases.

The particulate solid collection area 280 in the lower segment 272 may comprise a particulate solid outlet port 222. In one or more embodiments, the particulate solid outlet port 222 may be located proximate to, or even on, the central vertical axis 299. According to one or more embodiments, the bottom of the particulate solid collection area 280 may be curved such that the particulate solid outlet port 222 is located at the lowest portion of the particulate solid collection area 280. Standpipe 126 may be connected to the particulate solid separation section 210 at particulate solid outlet port 222, and the particulate solids may be transferred out of the reactor section 200 via standpipe 126 and into the regeneration section 300. Optionally, the particulate solids may also be transferred directly back into the reaction vessel 250 via standpipe 122. In such embodiments, standpipe 122 and standpipe 126 may each be offset from the central vertical axis 229. Alternatively, the particulate solids may be premixed with regenerated particulate solids in the transport riser 130.

Without wishing to be bound by theory, it is believed that when the riser 230 does not pass through the particulate solid collection area 280 and when the particulate solid outlet port 222 is located on the central vertical axis 299, then the flow of particulate solids through the particulate solid collection area 280 may be improved relative to designs in which the riser 230 does pass through the particulate solid collection area 280. When the riser 230 does not pass through the particulate solid collection area 280 and the riser port 218 is not located on the central vertical axis 299, the particulate solid outlet port 222 may be located on the central vertical axis 299. As such, the particulate solids may move through the particulate solid collection area 280 in manner more closely resembling plug flow. This may lead to an increased residence time of the particulate solids within the particulate solid collection area 280 which may be beneficial when stripping or other contemplated processes occur within the particulate solid collection area 280.

As described herein, portions of system units such as reaction vessel walls, separation section walls, or riser walls, may comprise a metallic material, such as carbon or stainless steel. In addition, the walls of various system units may have portions that are attached with other portions of the same system unit or to another system unit. Sometimes, the points of attachment or connection are referred to herein as "attachment points" and may incorporate any known bonding medium such as, without limitation, a weld, an adhesive, a solder, etc. It should be understood that components of the system may be "directly connected" at an attachment point, such as a weld.

To mitigate damage caused by hot particulate solids and gasses, refractory materials may be used as internal linings of various system components. Refractory materials may be included on the riser 230 as well as the particulate solid separation section 210. It should be understood that while embodiments are provided of specific refractory material arrangements and materials, they should not be considered limiting regarding the physical structure of the disclosed system. For example, refractory liner may extend in the riser 230 along an interior surface of the riser 230 and along interior surfaces of the middle segment 274 and upper segment 276 of the particulate solid separation section 210. The refractory liner may include hex mesh or other suitable refractory materials.

Mechanical loads applied onto the reaction vessel 250, and more specifically the connected vessel nozzles like 218, from the weight of the particulate solids and other parts of the reactor section 200 may be high, and springs may be utilized to allow vessel movement due to thermal differences in the vessel and piping walls. These springs may apply pressure upwardly on the reaction vessel 250 and nozzle 218 when the vessel is empty. When the vessel has an upset catalyst weight, the loads on nozzle 218 could shift downward. This design philosophy decreases the total load in either direction nozzle 218 would see. For example, the reaction vessel 250 may be hung from springs, or springs may be positioned below the reaction vessel 250 to support its weight, the catalyst weight, and to allow for thermal movements. For example, FIG. 1 depicts spring supports 188 mechanically attached to the reactor section 200 at the reaction vessel 250, wherein the reactor section 200 is suspended from a support structure by the spring supports 188.

Additionally, the reaction vessel 250 and riser 230 may undergo thermal expansion. As such, hanging the reaction vessel 250 from spring supports 188 or supporting the reaction vessel 250 with spring supports 188 may relieve tension between the reaction vessel 250 and the exterior riser segment 232. In place of springs, referring now to FIG. 2, an expansion joint 282 may be positioned between the reaction vessel 250 and the exterior riser segment 232. As described herein, an “expansion joint” may refer to a bellows made of metal or other suitable material, such as refractory, plastic, fiber, or an elastomer, which reduces the stress between the system components joined by the expansion joint. For example, expansion joints may be used to reduce stress between system components due to thermal expansion and contraction. In one or more embodiments, an expansion joint 282 may be used in combination with spring supports to mitigate stress caused by thermal expansion between the reaction vessel 250 and the exterior riser segment 232.

After separation in the particulate solid separation section 210, the spent particulate solids are transferred to the regeneration section 300. The regeneration section 300, as described herein, may share many structural similarities with the reactor section 200. As such, the reference numbers assigned to the portions of the regeneration section 300 are analogous to those used with reference to the reactor section 200, where if the final two digits of the reference number are the same the given portions of the reactor section 200 and regeneration section 300 may serve similar functions and have similar physical structure. Thus, many of the present disclosures related to the reactor section 200 may be equally applied to the regeneration section 300, and distinctions between the reactor section 200 and the regeneration section 300 will be highlighted hereinbelow.

Referring now to the regeneration section 300, as depicted in FIG. 1, the particulate solid treatment vessel 350 of the regeneration section 300 may include one or more reactor vessel inlet ports 352 and a reactor vessel outlet port 354 in fluid communication with, or even directly connected to the exterior riser segment 332 of the riser 330. The particulate solid treatment vessel 350 may be in fluid communication with the particulate solid separation section 210 via standpipe 126, which may supply spent particulate solids from the reactor section 200 to the regeneration section 300 for regeneration. The particulate solid treatment vessel 350 may include an additional reactor vessel inlet port 352 where gas inlet 128 connects to the particulate solid treatment vessel 350. The gas inlet 128 may supply reactive gases, such as supplemental fuel gasses and oxygen containing gasses, including air, which may be used to at least partially regenerate the particulate solids. In one or more embodiments, the particulate solid treatment vessel 350 may comprise multiple additional reactor vessel inlet ports, and each additional reactor vessel inlet port may supply a different reactive fluid to the particulate solid treatment vessel 350. For example, the particulate solids may be coked following the reactions in the reaction vessel 250, and the coke may be removed from the particulate solids by a combustion reaction. For example, oxygen containing gasses, such as air, may be fed into the particulate solid treatment vessel 350 via the gas inlet 128 to oxidize the particulate solids, or supplemental fuel may be fed into the particulate solid treatment vessel 350 and combusted to heat the particulate solids.

As depicted in FIG. 1, the particulate solid treatment vessel 350 may be directly connected to the exterior riser segment 332 of the riser 330. In one embodiment, the particulate solid treatment vessel 350 may include a particulate solid treatment vessel body section 356 and a particulate solid treatment vessel transition section 358. The particulate solid treatment vessel body section 356 may generally comprise a greater diameter than the particulate solid treatment vessel transition section 358, and the particulate solid treatment vessel transition section 358 may be tapered from the size of the diameter of the particulate solid treatment vessel body section 356 to the size of the diameter of the exterior riser segment 332 such that the particulate solid treatment vessel transition section 358 projects inwardly from the particulate solid treatment vessel body section 356 to the exterior riser segment 332.

It should be understood that the particulate solid treatment vessel 350 and the riser 330 may undergo thermal expansion and, as described hereinabove, may be supported by spring supports 188. Additionally, the particulate solid treatment vessel 350 may be joined to the riser 330 by an expansion joint in one or more embodiments. For example, an expansion joint may be positioned between the particulate solid treatment vessel 350 and the exterior riser segment 332.

Still referring to FIG. 1, the particulate solid separation section 310 includes an outer shell 312 defining an interior region 314 of the particulate solid separation section 310. The outer shell 312 may comprise a gas outlet port 316, a riser port 318, and a particulate solid outlet port 322. Furthermore, the outer shell 312 may house a gas/solids separation device 320 and a solid particulate collection area 380 in the interior region 314 of the particulate solid separation section 310.

Similar to the reactor section 200, the outer shell 312 of the particulate solid separation section 310 may define an upper segment 376, a middle segment 374, and a lower segment 372 of the particulate solid separation section 310, as described hereinabove regarding particulate solid separation section 210.

Referring again to FIG. 1, the riser 330 extends into the interior region 314 of the regeneration section 300 via a riser port 318. In one or more embodiments, the riser 330 may extend through the riser port 318 in a non-vertical direction. In one or more embodiments, the interior riser segment 334 does not pass through the lower segment 372 of the particulate solid separation section 310.

Referring to FIG. 1, the outer shell 312 may further house a riser termination device 378. The riser termination device may be positioned proximate to the interior riser segment 334. The gas and particulate solids passing through the riser 330 may be at least partially separated by riser termination device 378. The gas and remaining particulate solids may be transported to a secondary separation device 320 in the particulate solid separation section 310. The secondary separation device 320 may be any device suitable to separate solid particles from gasses, such as a cyclone or a series of cyclones, as described hereinabove regarding gas/solids separation device 220. The secondary separation device 320 may deposit separated particulate solids into the bottom of the upper segment 376, the middle segment 374 or the lower segment 372 of the particulate solid separation section 310.

As such, the particulate solids may flow by gravity from the bottom of the upper segment 376 or the middle segment 374 to the lower segment 372.

The lower segment 372 of the particulate solid separation section 310 may comprise a solid particulate collection area 380, which may allow for the accumulation of particulate solids in the lower segment 372. In one or more embodiments, the solid particulate collection area 380 may comprise one or more of an oxygen soak zone, an oxygen stripping zone, and a reduction zone. The solid particulate collection area 380 may further comprise a particulate solid outlet port 322 similar to particulate solid outlet port 222 described hereinabove.

In one or more embodiments, standpipe 124 may be in fluid communication with particulate solid outlet port 322, and regenerated particulate solids may be passed from the regeneration section 300 to the reactor section 200 through standpipe 124. As such, the particulate solids may be continuously recirculated through the reactor system 100.

EXAMPLES

The following examples illustrate features of the present disclosure but are not intended to limit the scope of the disclosure. The following examples discuss the performance of solid particulate collection areas according to one or more embodiments disclosed herein.

Example 1: Riser Residence Time and Propylene Selectivity

A reactor system according to embodiments disclosed hereinabove was modeled to analyze the effect of residence time in the riser on propylene selectivity during a propane dehydrogenation reaction. The modeling results comparing the change in riser residence time to the change in propylene selectivity are displayed in Table 1.

TABLE 1

| Δ Residence Time (seconds) | Δ Propylene Selectivity (mol %) |
|---|---|
| −0.51 | 0.31 |
| −0.76 | 0.44 |
| −1.27 | 0.75 |

As displayed in Table 1, as the residence time within the riser decreased, the propylene selectivity increased. This is likely due to the reduction in secondary reactions that may occur within the riser. As the residence time of the riser decreases, there is less opportunity for these side reactions to occur, which in turn results in an overall increase in the propylene selectivity of the system. As described hereinabove, utilizing a riser that enters the particulate solid separation section in a non-vertical orientation may allow the riser to be shorter. As such, the presently disclosed risers provide an advantage over conventional riser that enter the particulate solid separation section vertically through the bottom of the particulate solid separation section by having a shorter length, and thus, a shorter residence time during which undesired secondary reactions may occur.

Figure 4:
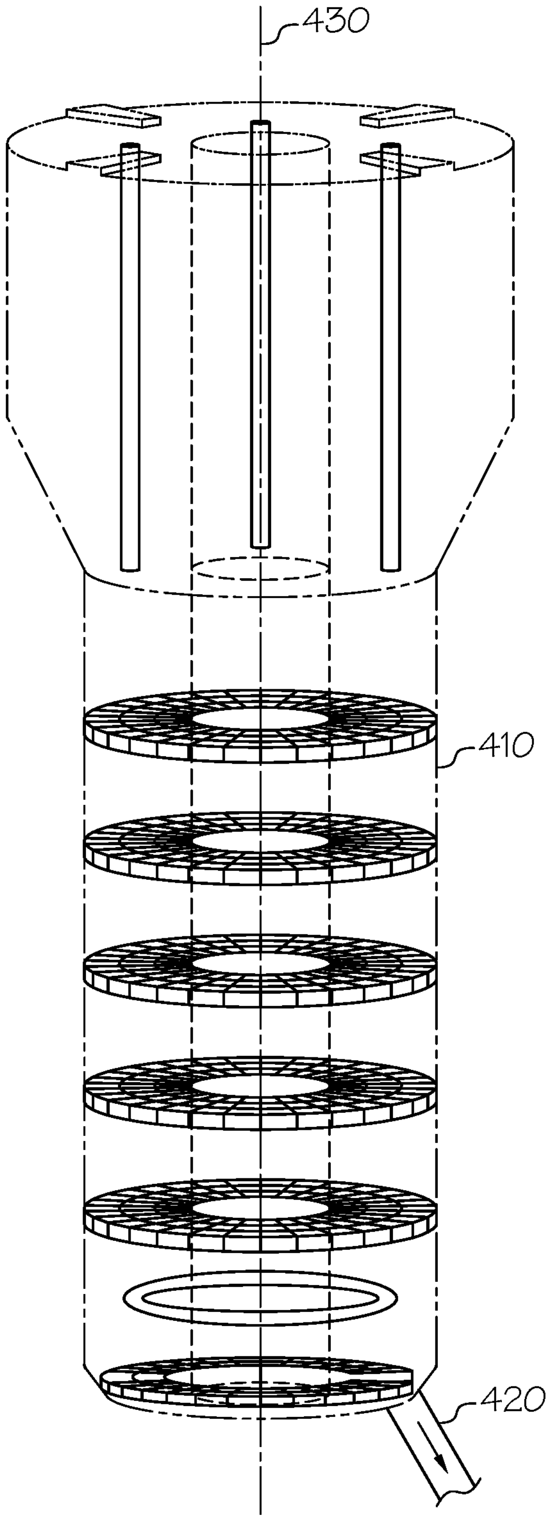
FIG. 4 depicts a solid particulate collection area, according to one or more embodiments disclosed herein.

Example 2: Flow of Particulate Solids Through Particulate Solid Collection Areas Flow of particulate solids through two particulate solid collection areas was modeled. The first particulate solid collection area 410 is depicted in FIG. 4, and had an annular shape with a single exit standpipe 420 located at the bottom of the particulate solid collection area 410. The exit standpipe 420 was not positioned on a central axis 430 of the first particulate solid collection area 410. The first particulate solid collection area 410 also includes several chordal beam supports covered with subway grating 440.

Figure 5:
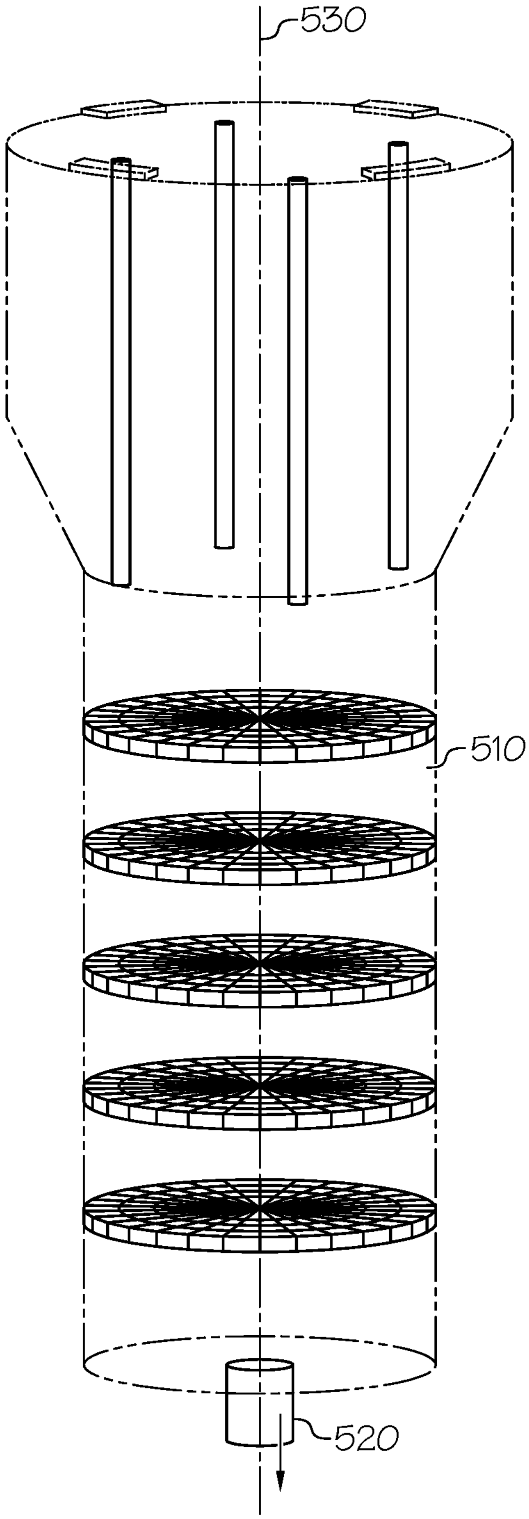
FIG. 5 depicts a solid particulate collection area, according to one or more embodiments disclosed herein.

The second particulate solid collection area 510 is depicted in FIG. 5, and had a cylindrical shape and an exit standpipe 520 located at the bottom of the particulate solid collection area 510. The exit standpipe 520 was positioned on a central axis 530 of the second particulate solid collection area 510. The second particulate solid collection area 510 also includes several chordal beam supports covered with subway grating 540.

Computational fluid dynamics (CFD) simulations were conducted to model the flow of particulate solids through the first and second particulate solid collection areas. As such, solid residence time distributions (RTD) in each vessel were obtained. For the purposes of the simulation, the diameter of each of the first and second particulate solid collection areas was set to 46 inches. The superficial gas velocity at the bottom of each vessel was 0.3 ft/sec and the average particulate solid flux was 3.4 $lb/ft^2$-sec. Additionally, the average turnaround time for the particulate solids was 8 minutes.

The CFD simulation for the first particulate solid collection area predicted that that the shortest residence time of the particulate solids was about 30 seconds, due to short-circuiting of the particulate solids on the outlet standpipe side of the vessel. The CFD simulation also predicted that about 42% of the particulate solids had a residence time of less than 4 minutes. The CFD simulations for the second particulate solid collection area predicted that the shortest residence time for the particulate solids would be greater than 1 minute and that only 30% of the particulate solids had a residence time shorter than 4 minutes.

Figure 6:
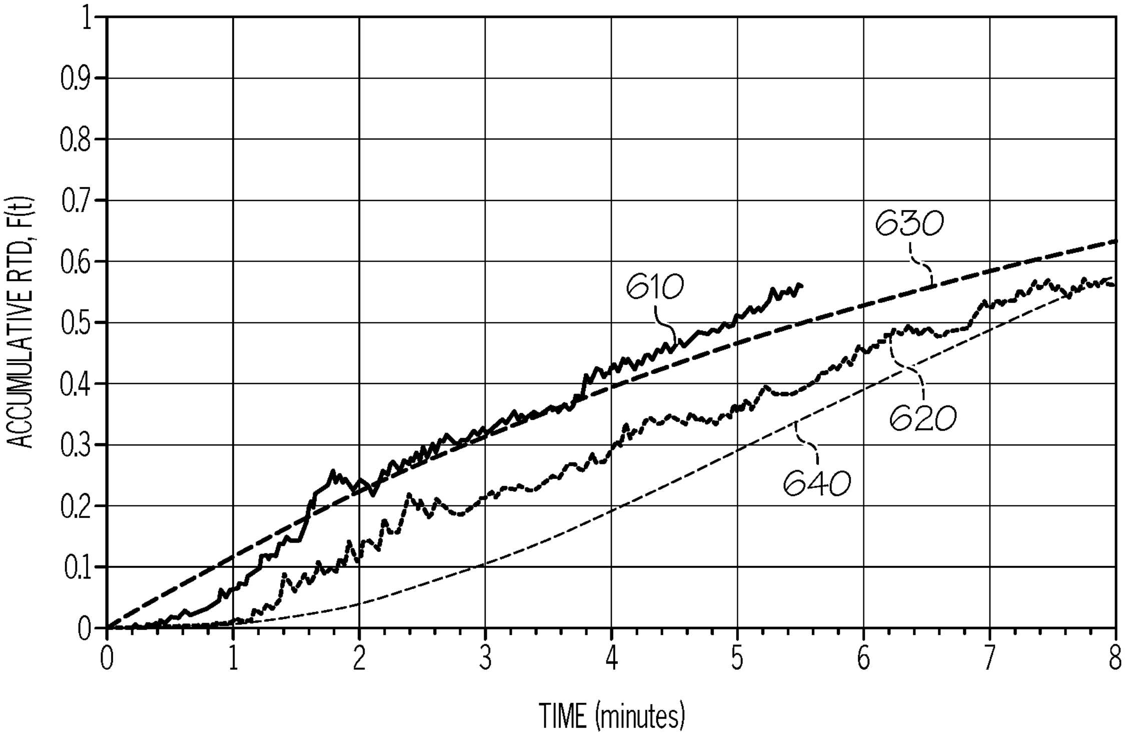
FIG. 6 graphically depicts residence time distributions for solid particulate collection areas, according to one or more embodiments disclosed herein.

The RTDs for the first and second particulate solid collection areas are graphically depicted in FIG. 6. The RTD for the first particulate solid collection area is depicted by line 610 and the RTD for the second particulate solid collection area is depicted by line 620. Additionally, RTDs for one continuous stirred tank reactor (CSTR) and three CSTRs in series are displayed in FIG. 6 for reference. The RTD for one CSTR is depicted by line 630 and the RTD for three CSTRs in series is depicted by line 640. As displayed in FIG. 6, the RTD for the first particulate solid collection area is comparable to the RTD for a single CSTR and the RTD for the second particulate solid collection area is comparable to the RTD for three CSTRs in series. The second particulate solid collection area provides a benefit over the first particulate solid collection area because the flow of particulate solids through the second particulate solid collection area more closely resembles plug flow. As such, fewer particulate solids exit the particulate solid collection area quickly and fewer particulate solids are retained in the particulate solid collection area for a long time. This results in more consistent treatment of particulate solids in the particulate solid collection area.

In a first aspect of the present disclosure, olefins may be produced by a method comprising contacting a hydrocarbon feed stream with a particulate solid in a reaction vessel. Contacting the hydrocarbon feed stream with the particulate solid may react the hydrocarbon feed stream to form an olefin-containing product stream. The reaction vessel may be connected to a riser, and the reaction vessel may have a maximum cross sectional area that is at least 3 times the maximum cross sectional area of the riser. The method may further comprise passing the particulate solid through the riser. The riser may extend through a riser port of an outer shell of a particulate solid separation section such that the riser may comprise an interior riser segment positioned in an interior region of the particulate solid separation section and an exterior riser segment positioned outside of an outer shell of the particulate solid separation section. The particulate solid separation section may comprise at least an outer shell defining an interior region of the particulate solid separation section. The outer shell may comprise a gas outlet port, a riser port, and a particulate solid outlet port. The outer shell may house a gas/solids separation device and a solid particulate collection area in the interior region of the particulate solid separation section. The riser port may be positioned on a sidewall of the outer shell such that it is not located on a central vertical axis of the particulate solid separation section. The method may further comprise separating the particulate solid from the olefin-containing product stream in the gas/solids separation device and passing the particulate solids, separated from the olefin-containing product stream, to the solid particulate collection area located proximate the central vertical axis of the particulate solid separation section.

A second aspect of the present disclosure may include the first aspect where the riser extends through the riser port in a non-vertical direction.

A third aspect of the present disclosure may include either of the first or second aspects where the riser extends through the riser port in a diagonal direction, wherein the diagonal direction is from 15 to 75 degrees from vertical.

A fourth aspect of the present disclosure may include any of the first through second aspects where the riser extends through the riser port in a substantially horizontal direction.

A fifth aspect of the present disclosure may include any of the first through fourth aspects where the interior riser segment comprises a vertical portion, a non-vertical portion proximate the riser port, and a non-linear portion connecting the vertical portion and the non-vertical portion.

A sixth aspect of the present disclosure may include any of the first through fifth aspects where the exterior riser segment comprises a vertical portion proximate to the reaction vessel, a non-vertical portion proximate to the riser port, and a non-linear portion connecting the vertical portion and the non-vertical portion.

A seventh aspect of the present disclosure may include any of the first through sixth aspects where the reaction vessel operates as a fast fluidized, turbulent, or bubbling bed reactor and the riser operates as a dilute phase riser reactor.

An eighth aspect of the present disclosure may include any of the first through seventh aspects where the maximum cross sectional area of the outer shell of the upper particulate solids separation section is from 5 to 40 times the maximum cross sectional area of the riser.

A ninth aspect of the present disclosure may include any of the first through eighth aspects where the reaction vessel comprises a reaction vessel body section and a reaction vessel transition section, wherein the reaction vessel transition section is positioned between the reaction vessel body section and the exterior riser segment.

A tenth aspect of the present disclosure may include the ninth aspect where the reaction vessel body section has a diameter and a height, wherein a ratio of the diameter to the height of the reaction vessel body section is from 5:1 to 1:5.

An eleventh aspect of the present disclosure may include any of the first through tenth aspects where the reaction vessel is supported by spring supports.

A twelfth aspect of the present disclosure may include any of the first through eleventh aspects where the reaction vessel is connected to a vertical portion of the exterior riser segment by an expansion joint.

A thirteenth aspect of the present disclosure may include any of the first through twelfth aspects where the gas/solids separation device comprises one or more cyclones.

A fourteenth aspect of the present disclosure may include any of the first through thirteenth aspects where the riser does not pass through the solid particulate collection area.

A fifteenth aspect of the present disclosure may include any of the first through fourteenth aspects where the solid particulate collection area comprises a stripper.

The subject matter of the present disclosure has been described in detail and by reference to specific embodiments. It should be understood that any detailed description of a component or feature of an embodiment does not necessarily imply that the component or feature is essential to the particular embodiment or to any other embodiment. Further, it should be apparent to those skilled in the art that various modifications and variations can be made to the described embodiments without departing from the spirit and scope of the claimed subject matter.

For the purposes of describing and defining the present disclosure it is noted that the terms "about" or "approximately" are utilized in this disclosure to represent the inherent degree of uncertainty that may be attributed to any quantitative comparison, value, measurement, or other representation. The terms "about" and/or "approximately" are also utilized in this disclosure to represent the degree by which a quantitative representation may vary from a stated reference without resulting in a change in the basic function of the subject matter at issue.

It is noted that one or more of the following claims utilize the term "wherein" as a transitional phrase. For the purposes of defining the present technology, it is noted that this term is introduced in the claims as an open-ended transitional phrase that is used to introduce a recitation of a series of characteristics of the structure and should be interpreted in like manner as the more commonly used open-ended preamble term "comprising."

It should be understood that where a first component is described as "comprising" a second component, it is contemplated that, in some embodiments, the first component "consists" or "consists essentially of" that second component. It should further be understood that where a first component is described as "comprising" a second component, it is contemplated that, in some embodiments, the first component comprises at least 10%, at least 20%, at least 30%, at least 40%, at least 50%, at least 60%, at least 70%, at least 80%, at least 90%, at least 95%, or even at least 99% that second component (where % can be weight % or molar %).

Additionally, the term "consisting essentially of" is used in this disclosure to refer to quantitative values that do not materially affect the basic and novel characteristic(s) of the disclosure. For example, a chemical composition "consisting essentially" of a particular chemical constituent or group of chemical constituents should be understood to mean that the composition includes at least about 99.5% of a that particular chemical constituent or group of chemical constituents.

It should be understood that any two quantitative values assigned to a property may constitute a range of that property, and all combinations of ranges formed from all stated quantitative values of a given property are contemplated in this disclosure. It should be appreciated that compositional ranges of a chemical constituent in a composition should be appreciated as containing, in some embodiments, a mixture of isomers of that constituent. In additional embodiments, the chemical compounds may be present in alternative forms such as derivatives, salts, hydroxides, etc.

The invention claimed is:

1. A method for producing olefins, the method comprising:

contacting a hydrocarbon feed stream with a particulate solid in a reaction vessel thereby reacting the hydrocarbon feed stream to form an olefin-containing product stream, wherein:

the reaction vessel is connected to a riser, the reaction vessel has a maximum cross sectional area that is at least 3 times a maximum cross sectional area of the riser, the reaction vessel operates as a fast fluidized, turbulent, or bubbling bed reactor and the riser operates as a dilute phase riser reactor, the hydrocarbon feed stream comprises one or more of ethyl benzene, ethane, propane, n-butane, i-butane, methanol, ethanol, propanol, or butanol, and the reacting comprises one or more of dehydrogenation reactions, dehydration reactions, and methanol-to-olefin reactions;

passing the particulate solid through the riser, the riser extending through a riser port of an outer shell of a particulate solid separation section such that the riser comprises an interior riser segment positioned in an interior region of the particulate solid separation section and an exterior riser segment positioned outside of the outer shell of the particulate solid separation section, wherein the particulate solid separation section comprises at least the outer shell defining an interior region of the particulate solid separation section, the outer shell comprising a gas outlet port, a riser port, and a particulate solid outlet port, and wherein the outer shell houses a gas/solids separation device and a solid particulate collection area in the interior region of the particulate solid separation section, and wherein the riser port is positioned on a sidewall of the outer shell such that it is not located on a central vertical axis of the particulate solid separation section;

separating the particulate solid from the olefin-containing product stream in the gas/solids separation device; and passing the particulate solid, separated from the olefin-containing product stream, to the solid particulate collection area located proximate the central vertical axis of the particulate solid separation section.

2. The method of claim 1, wherein the riser extends through the riser port in a non-vertical direction.

3. The method of claim 1, wherein the riser extends through the riser port in a diagonal direction, wherein the diagonal direction is from 15 to 75 degrees from vertical.

4. The method of claim 1, wherein the riser extends through the riser port in a substantially horizontal direction.

5. The method of claim 1, wherein the interior riser segment comprises a vertical portion, a non-vertical portion proximate the riser port, and a non-linear portion connecting the vertical portion and the non-vertical portion.

6. The method of claim 1, wherein the exterior riser segment comprises a vertical portion proximate to the reaction vessel, a non-vertical portion proximate to the riser port, and a non-linear portion connecting the vertical portion and the non-vertical portion.

7. The method of claim 1, wherein a maximum cross sectional area of the outer shell of the particulate solids separation section is from 5 to 40 times the maximum cross sectional area of the riser.

8. The method of claim 1, wherein the reaction vessel comprises a reaction vessel body section and a reaction vessel transition section, wherein the reaction vessel transition section is positioned between the reaction vessel body section and the exterior riser segment.

9. The method of claim 8, wherein the reaction vessel body section has a diameter and a height, wherein a ratio of the diameter to the height of the reaction vessel body section is from 5:1 to 1:5.

10. The method of claim 1, wherein the reaction vessel is supported by spring supports.

11. The method of claim 1, wherein the reaction vessel is connected to a vertical portion of the exterior riser segment by an expansion joint.

12. The method of claim 1, wherein the gas/solids separation device comprises one or more cyclones.

13. The method of claim 1, wherein the riser does not pass through the solid particulate collection area.

14. The method of claim 1, wherein the solid particulate collection area comprises a stripper.

15. The method of claim 1, wherein the particulate solid passes through the riser to the gas/solids separation device.

16. The method of claim 1, wherein the reacting comprises one or both of dehydrogenation reactions and dehydration reactions.

17. The method of claim 1, wherein the olefin-containing product stream comprises at least 50 wt. % of light olefins.

18. The method of claim 1, wherein:

the hydrocarbon feed stream comprises one or more of ethyl benzene, ethane, propane, or n-butane; and the reacting comprises one or both of dehydrogenation reactions and dehydration reactions.

* * * * *